United States Patent [19]

Palomo Coll

[11] Patent Number: 5,292,886
[45] Date of Patent: Mar. 8, 1994

[54] PROCESS FOR THE PREPARATION OF 2-HALOMETHYL-3,5-DIMETHYL-4-METHOXYPYRIDINE HALOHYDRATE

[76] Inventor: Alberto Palomo Coll, Doctor Carulla 10, 08017-Barcelona, Spain

[21] Appl. No.: 796,070

[22] Filed: Nov. 20, 1991

[30] Foreign Application Priority Data

Dec. 5, 1990 [ES] Spain .................................. 9003113

[51] Int. Cl.$^5$ .......................................... C07D 213/89
[52] U.S. Cl. .................................................. 546/303
[58] Field of Search ............................. 546/303, 271

[56] References Cited

U.S. PATENT DOCUMENTS 5,066,810 11/1991 Baumann .............................. 546/303

FOREIGN PATENT DOCUMENTS 0103353 3/1984 European Pat. Off. ............ 546/303
0173664 3/1986 European Pat. Off. ............ 546/271
0268956 6/1988 European Pat. Off. ............ 546/303

OTHER PUBLICATIONS

March, *Advanced Organic Chemistry*, pp. 382–384 3rd Ed. 1985.
Journal of Organic Chemistry, vol. 33, No. 4, Apr. 1968; pp. 1530–1532.

*Primary Examiner*—C. Warren Ivy
*Assistant Examiner*—Zinna N. Davis

[57] ABSTRACT

The process comprises a first step of O-acylation and subsequent acyloxylation of the 2-position methyl group of 2,3,5-trimethyl-4-methoxypyridine N-oxide, to obtain a compound which is subjected to a final halogenation step, in which the 2-position substituent is converted into halomethyl with a halogenating agent.

12 Claims, 5 Drawing Sheets

PROCESS FOR THE PREPARATION OF 2-HALOMETHYL-3,5-DIMETHYL-4-METHOXYPYRIDINE HALOHYDRATE

BACKGROUND OF THE INVENTION

Field of the Invention

The invention relates to a process for the preparation of 2-halomethyl-3,5-dimethyl-4-methoxypyridine halohydrate, of formula I

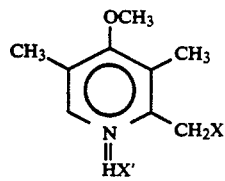

where X and X' are halogens, the same or different.

Said compound is a precursor of the synthesis of omeprazol, the chemical name of which is 5-methoxy-2-(((3,5-dimethyl-4-methoxy-2-pyridinyl)methyl)sulphinyl)-1H-benzimidazole, of formula II

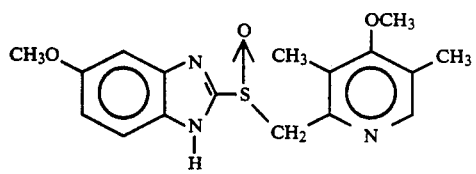

Omeprazol is a very effective drug for the treatment of gastric ulcers.

SUMMARY OF THE INVENTION

The present invention is characterised in that it comprises the following steps:

a first step of O-acylation and subsequent acyloxylation of the 2-position methyl group in of 2,3,5-trimethyl-4-methoxypyridine N-oxide, of formula III

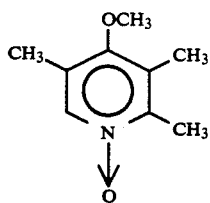

by treatment with an acylating agent, to obtain a compound of formula IV

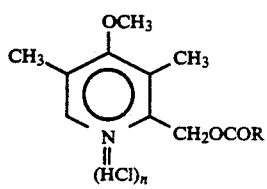

where R is a methyl, trichloromethyl or trifluoromethyl group and n is 0 or 1;

and a final halogenation step in which the 2-position substituent is converted into halomethyl with a halogenating agent, to give the compound of formula I.

According to the invention, the acylating agent is an acid anhydride, giving 2-acyloxymethyl-3,5-dimethyl-4-methoxypyridine of formula IVa

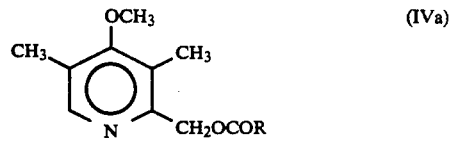

Alternatively, according to the invention, said acylating agent is an acid chloride, giving 2-acyloxymethyl-3,5-dimethyl-4-methoxypyridine hydrochloride of formula IVb

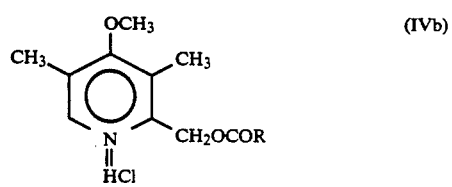

According to a further feature of the invention, there is inserted between the first and final steps, a base hydrolysis step of the formula IV compound, by way of an aqueous alkaline hydroxide, to give 2-hydroxymethyl-3,5-dimethyl-4-methoxypyridine of formula Va

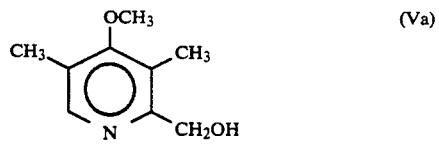

chlorination of which with amidinium chloride gives 2-chloromethyl-3,5-dimethyl-4-methoxypyridine hydrochloride of formula VI

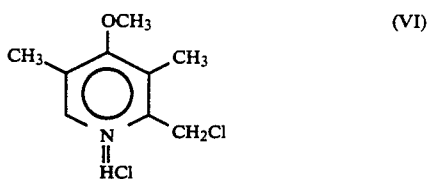

In a further alternative feature of the above, there is inserted between the first and final step an acid hydrolysis step of the formula IV compound with hydrochloric acid to give 2-hydroxymethyl-3,5-dimethyl-4-methoxypyridine hydrochloride of formula Vb

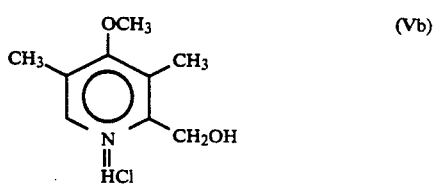

chlorination of which with amidinium chloride gives the hydrochloride of formula VI.

Also according to the invention, after the first step of O-acylation and subsequent acyloxylation, the halogenation step in which the acyloxy radical -OCOR is replaced with a halogen is carried out.

According to the literature, the synthesis of 2-chloromethyl-3,5-dimethyl-4-methoxypyridine hydrochloride of formula VI, from the formula III compound is effected in three chemical steps corresponding to the above mentioned O-acylation and subsequent acyloxylation, hydrolysis and halogenation steps (Spanish patent 525,122 and EP 0 103 553).

The reaction of the first step is carried out with treatment of the formula III compound with acetic anhydride in acetic acid at a temperature of 130° C., followed by isolation of the compound thus obtained by extraction with CH₂Cl₂. The yield of this reaction is not described.

Research conducted in connection with the present invention has revealed that, on an industrial scale, the treatment described in the foregoing paragraph leads to indeterminable and unforeseeable yields and, also, to intense black colouring of the crude reaction product, which hinders the visibility of the interphases during the extractions.

The invention contemplates that the compound of formula VII,

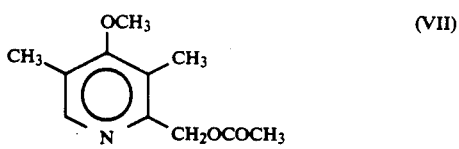

be synthesised by treatment of the formula III compound with acetic anhydride in the presence of a 4-dialkylaminopyridine such as 4-dimethylaminopyridine, 4-guanidinepyridine or 4-pyrrolidinepyridine (compounds described in Spanish patent 550,895, of which the present inventor is proprietor and inventor). The acylating agent is used in excess, possibly in the presence of a cosolvent such as acetic acid or chloroform.

It has been checked on a laboratory and pilot plant scale that the reaction is exothermic and may be carried out at a temperature ranging from 80° to 100° C., giving fully reproducible almost quantitative yields, with pale colouring. It should be highlighted that, in the absence of a catalyst, the results are always much less satisfactory, as already mentioned above.

Finally, the addition of the amount of water required to destroy the excess acetic anhydride and the subsequent distillation of acetic acid lead to a crude product which may be used directly as a starting product for step b). This process avoids the said isolation by extraction, which is operatively more laborious.

The hydrolysis step is described in the literature as being carried out with aqueous sodium hydroxide under reflux. The alcohol obtained is purified by distillation, thereby generating a large amount of resinous residue. The joint yield of the first and hydrolysis steps, carried out under the conditions described in the literature, is scarcely 40% on a laboratory scale (Spanish patent 525,122 and EP 0 103 553).

In the present invention, the base hydrolysis step is carried out in the presence of a cosolvent such as isopropyl alcohol under gentle pH (between 11 and 13) and temperature (from 0° to 75° C.) conditions, thereby notably reducing the resinous residue obtained in the said distillation. The yield of this reaction, when carried out at 25° C. and pH 12, is 92%.

The hydrolysis step may also be carried out with hydrochloric acid, giving the hydrochloride of formula Vb in solid form, which is isolated directly by filtration or centrifugation and which does not need any subsequent purification.

The literature does not provide any information on the physical and chemical reaction conditions for the chlorination step of the formula Va and Vb compounds.

These reaction conditions are described for the first time in this invention. To be precise, the chlorination step on the formula Va and Vb compounds is carried out at room temperature with amidinium chlorides formed in situ by treatment of thionyl chloride with an amide such as N,N-dimethylformamide (the isolation of said amidinium chlorides is described in Spanish patent 9000977, of which the present inventor is proprietor and inventor).

The product formed may be isolated by partial distillation of the solvent, addition of ethyl acetate and filtration. A white solid of high purity is obtained, corresponding to the formula VI compound, with an 86% yield.

The synthesis sequence described in the foregoing paragraphs is not, however, the only possible synthesis route for the formula I compound. Thus, a detailed examination of such sequence has suggested that one of the chemical steps thereof, the hydrolysis, may not be strictly necessary.

The direct nucleophilic substitution of the acetoxy group of the formula VII compound by a halogen to obtain the formula I compound is not described in the literature.

In the present invention, this direct substitution of the acyloxy radical by the halogen group is carried out with boron trihalogenides or with trimethylsilane iodide in a solvent such as methylene chloride. These reactions are based on an application of the articles "Chem. Comm." 667 (1971 and "Tetrahedron Lett." 22, 3915 (1981).

This direct substitution of the acyloxy radical may also be effected with the use of hydrogen chloride as reactant. In this case, the reaction almost certainly proceeds by way of an intramolecular nucleophilic substitution mechanism, with previous attack of the chloride anion on the carbonyl group. Since said chloride anion is a poor nucleophile, the reaction only takes place if said carbonyl group is highly activated, such as is the case of the formula VIII compound.

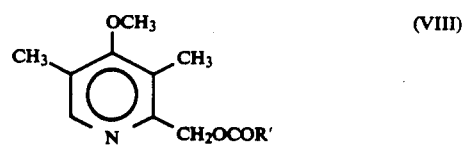

where R' is a trichloromethyl or trifluoromethyl group. The formula VII compound is insufficiently activated for the said reactant.

In the present invention, the formula VIII compound (or the hydrochloride thereof) is prepared from the formula III compound by treatment with the appropriate acid anhydride (trichloroacetic or trifluoroacetic anhydride) under conditions similar to those described for the preparation of the formula VII compound, i.e., in the presence of a 4-dialkylaminopyridine, such as 4-dimethylaminopyridine and a solvent such as chloroform.

The acid anhydrides described in the foregoing paragraph may be easily prepared according to the process described by the present inventor in the article published in "Afinidad", 405, 421 (1986).

The hydrochloride of the formula VIII compound is prepared preferably by reacting the formula III compound with trichloroacetyl chloride in an organochlorinated solvent, such as chloroform, possibly in the presence of catalytic traces of gamma-picoline.

Of course, the formula VIII compound (or the hydrochloride thereof) may be converted into the formula I compound in a similar way to the formula VII compound, although this possibility obviously does not represent any advantage.

On the other hand, the use of hydrogen chloride for said conversion is advantageous, since the halogenating agent is comparatively cheap.

This reaction, based on an application of the article "J. Org. Chem.", 33, 1530 (1968), is carried out in a solvent such as acetonitrile or chloroform at the reflux temperature of the mixture. The hydrogen chloride is introduced into the reaction medium as a gas current or as the hydrochloride of a weak organic base. This organic base is an ether such as dioxane, an amide such as dimethylformamide or the formula VIII compound itself.

To summarize, the process for preparing the 2-halomethyl-3,5-dimethyl-4-methoxypyridine halohydrate of formula I, describe herein, is characterised in that it comprises 2 or 3 chemical steps, the first of which is always the reaction of 2,3,5-trimethyl-4-methoxypyridine N-oxide, of formula III, with an acylating agent, and the final one is a nucleophilic substitution by halogen, preceded or not by hydrolysis.

According to one feature of the present invention, the acylating agent in the first step is trichloroacetyl chloride, possibly in the presence of gamma-picoline as catalyst, or it is an acid anhydride, preferably acetic anhydride, trifluroacetic anhydride or trichloroacetic anhydride, in the presence of a catalyst, preferably 4-dimethylaminopyridine, 4-guanidinepyridine or 4-pyrrolidinepyridine.

Where the said acylating agent is acetic anhydride, the reaction is preferably carried out at a temperature ranging from 80° to 120° C. and, possibly in the presence of a cosolvent such as acetic acid or chloroform. For the remaining acylating agents mentioned, the reaction is carried out preferably in chloroform at the reflux temperature of the mixture.

According to a further feature of the invention, the hydrolysis step is carried out in an acid medium, with hydrochloric acid, or in a basic medium with an aqueous alkaline hydroxide, under gentle pH (between 11 and 13) and temperature (between 0° and 75° C.) conditions, in the presence of a cosolvent such as isopropyl alcohol.

According to the invention, the halogenation step of the formula Va or Vb compounds is carried out with an amidinium chloride formed in situ by reacting thionyl chloride with an amide such as dimethylformamide, said amide being present in catalytic or stoichiometric amounts.

According to a final feature of the present invention, the direct substitution of the acyloxy radical by halogen is carried out with boron trihalogenide or trimethylsilane iodide, preferably in methylene chloride solution, or it is carried out, when the starting product is the formula VIII compound, with hydrogen chloride which is introduced into the reaction medium as a gas current or as the hydrochloride of a weak organic base. Said organic base is preferably an ether such as dioxane, an amide such as dimethylformamide or the formula VIII compound itself.

BRIEF DESCRIPTION OF THE DRAWINGS

The present description is accompanied by figures.

Figure 1:
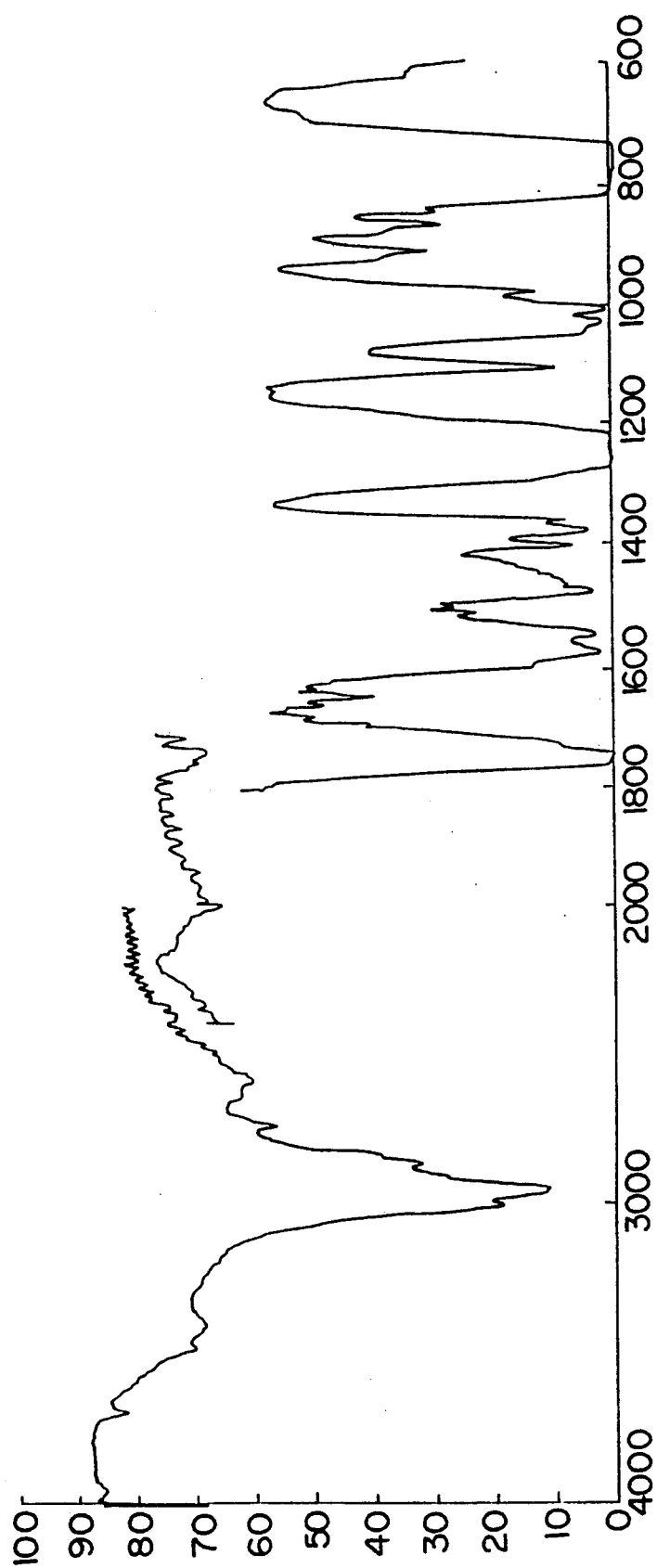
FIG. 1 to 3 respectively show the infra red spectra of 2-acetoxymethyl-3,5-dimethyl-4-methoxypyridine (FIG. 1); 2-hydroxymethyl-3,5-dimethyl-4-methoxypyridine (FIG. 2); 2-chloromethyl-3,5-dimethyl-4-methoxypyridine hydrochloride (FIG. 3). These spectra are shown in Cartesian graphs, where the x-axes give the wave number in $cm^{-1}$ and the y-axes give the percentage transmission. These spectra show the high purity of the products prepared according to the invention.
Figure 2:
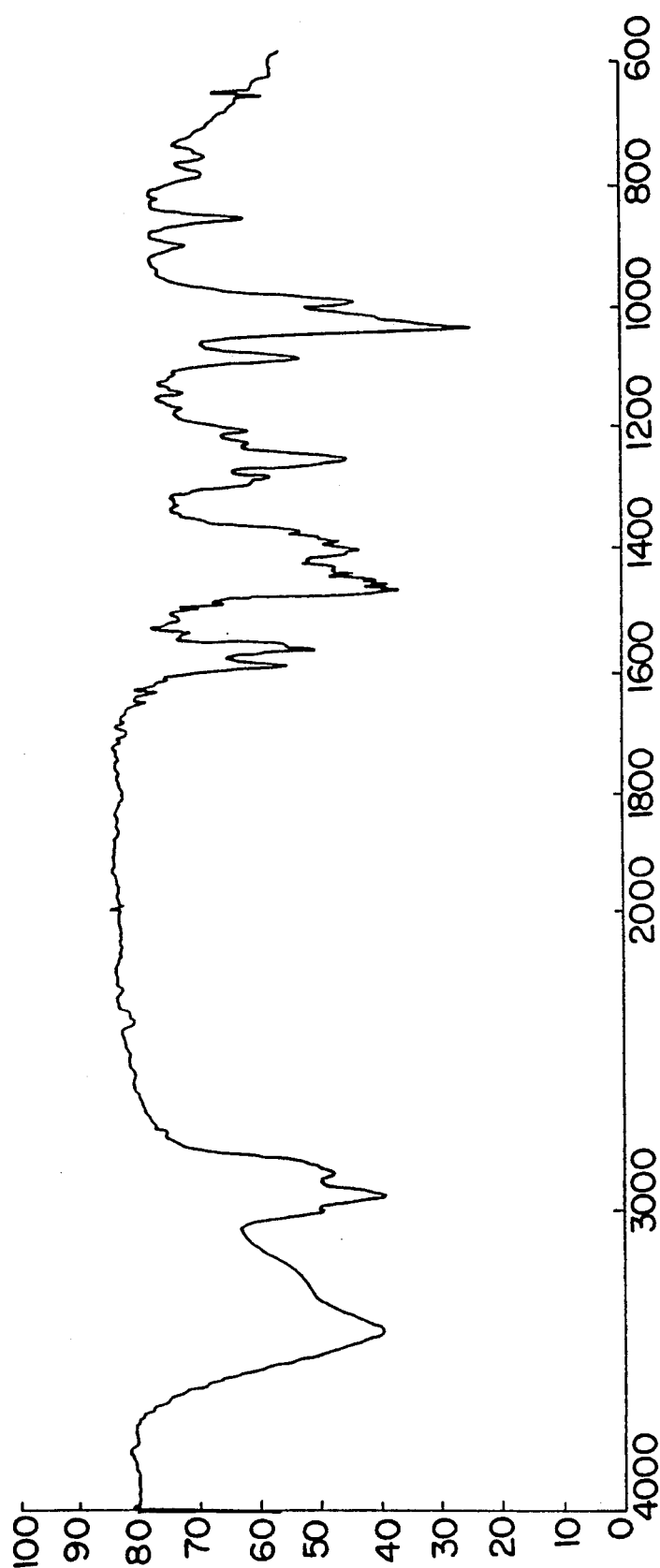
Figure 3:
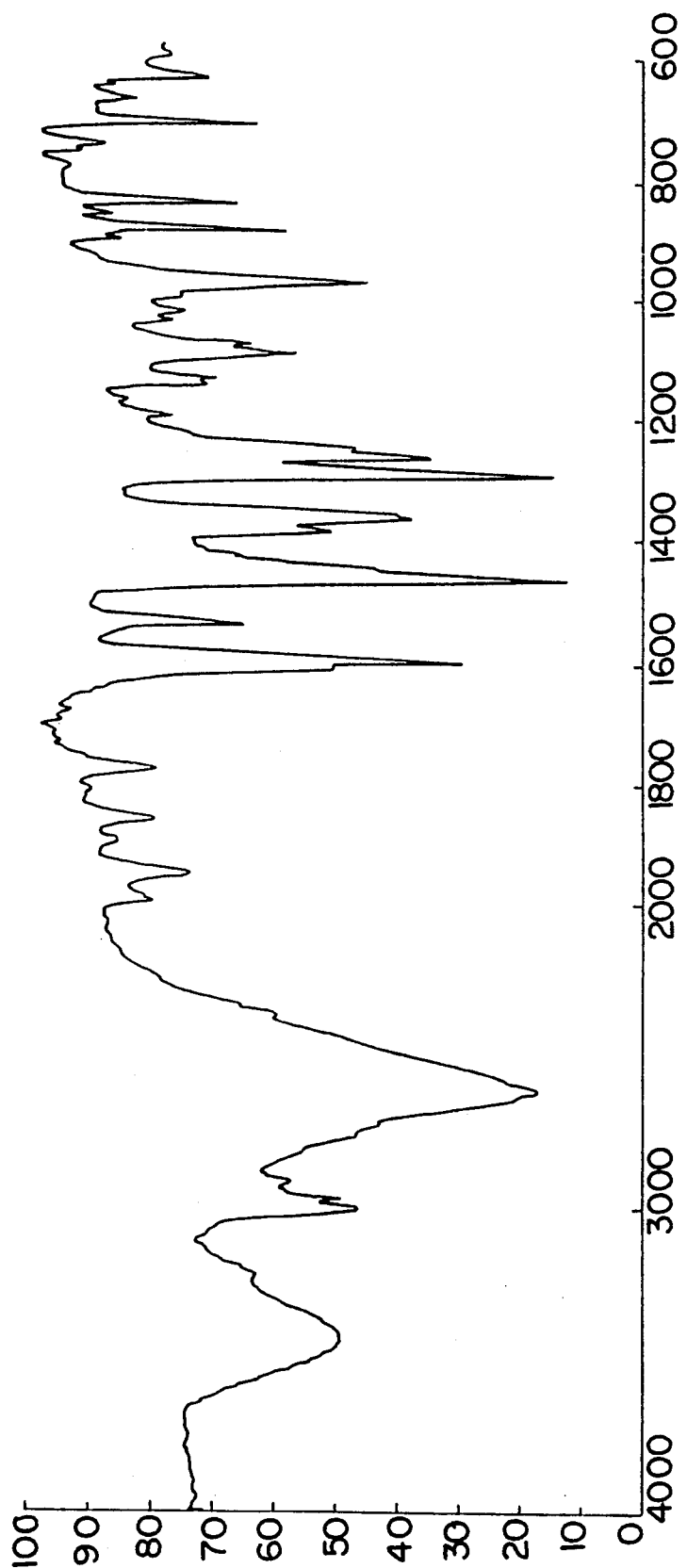
Figure 4:
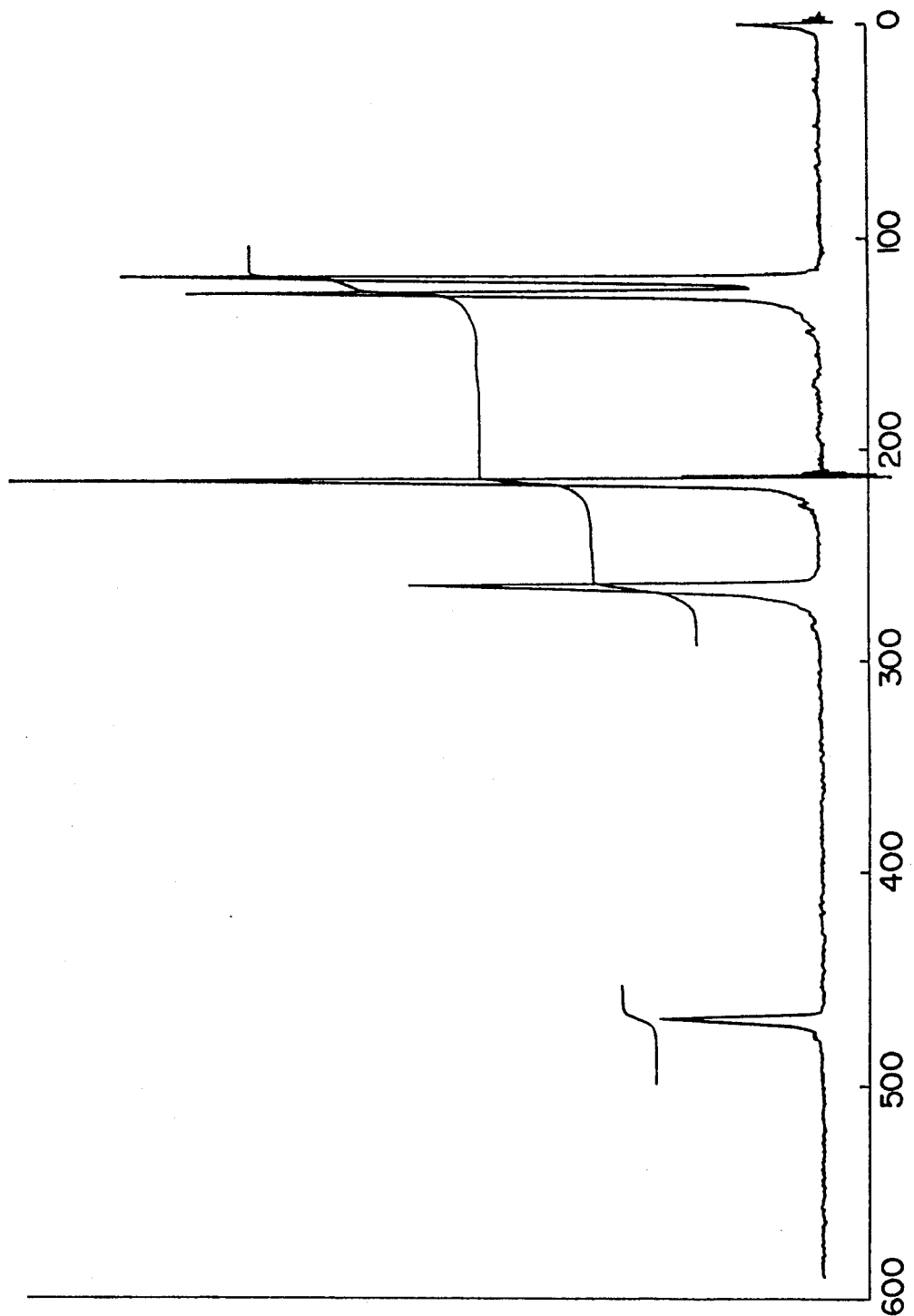
Figure 5:
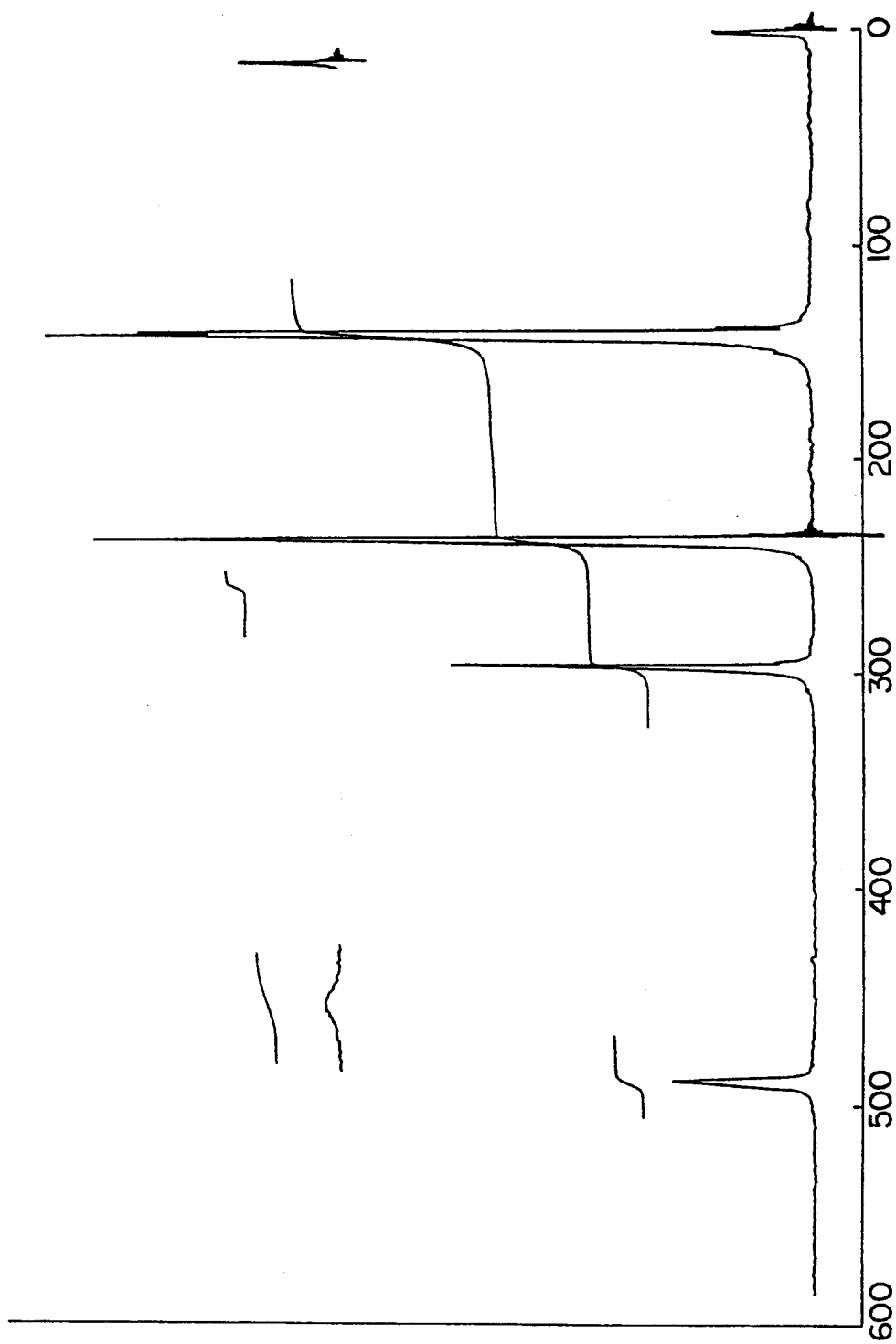

The remaining figures show the $^1$H-NMR spectra of 2-hydroxymethyl-3,5-dimethyl-4-methoxypyridine (FIG. 4); 2-chloromethyl-3,5-dimethyl-4-methoxypyridine hydrochloride (FIG. 5). These spectra are shown in Cartesian graphs where the x-axes give the magnetic field in cycles per second (Hz).

EXAMPLE 1

2-ACETOXYMETHYL-3,5-DIMETHYL-4-METHOXYPYRIDINE

A solution of 30.06 g (0.18 mole) of 2,3,5-trimethyl-4-methoxypyridine N-oxide in 100 ml of methylene chloride was added slowly (over approximately one hour) over a solution of 0.38 g of dimethylaminopyridine in 53.4 ml (0.565 mole) of acetic anhydride, heated to 90°–95° C., with the temperature being held within the abovementioned range and the methylene chloride being removed by distillation. At the end of the addition, the distillation was continued for a further 10 minutes, the mixture was cooled to below 90° C. and 7.5 ml of water were added slowly, holding the temperature below 90° C. Crude 2-acetoxymethyl-3,5-dimethyl-4-methoxypyridine was obtained by distillation at reduced pressure and was used directly as starting product for the hydrolysis (Example 2).

EXAMPLE 2

2-HYDROXYMETHYL-3,5-DIMETHYL-4-METHOXYPYRIDINE

30% aqueous sodium hydroxide was added over a solution of crude 2-acetoxymethyl-3,5-dimethyl-4-methoxypyridine prepared from 30.06 g (0.18 mole) of 2,3,5-trimethyl-4-methoxypyridine N-oxide, to pH 13. The mass was stirred for about 3.5 hours at 25°–28° C., with addition of 30% aqueous sodium hydroxide at the appropriate rate to hold the pH to between 11.7 and 13. Once the reaction was terminated (complete disappearance of the band located towards 1700 $cm^{-1}$) the pH was adjusted to 6.5 with acetic acid, water was added and the mass was extracted with methylene chloride. The solvent was removed by vacuum distillation and finally 2-hydroxymethyl-3,5-dimethyl-4-methoxypyridine was distilled at 142°–145° C. (9 torr.) as a colourless liquid which crystallised on standing. 27.23 g were obtained. Yield 92.4%.

EXAMPLE 3

2-CHLOROMETHYL-3,5-DIMETHYL-4-METHOXYPYRIDINE HYDROCHLORIDE 27.17 g (0.163 mole) of 2-hydroxymethyl-3,5-dimethyl-4-methoxypyridine were dissolved in 48 ml of methylene chloride, 1.7 ml of dimethylformamide were added and thereafter 17.3 ml (0.238 mole) of thionyl chloride were added over 25 minutes, while holding the temperature to 25°-28° C. Stirring was continued for a further 15 minutes at 20°-25° C. and the CH₂Cl₂ was removed by distillation until a thick paste was formed. 96 ml of ethyl acetate were added, the temperature was allowed to reach room temperature and stirring was continued for 15 minutes. The mixture was filtered and washed with ethyl acetate, to give 31.06 g of a white solid. Yield 86%.

I claim:

1. A process for the preparation of 2-chloromethyl-3,5-dimethyl-4-methoxypyridine hydrochloride of formula VI

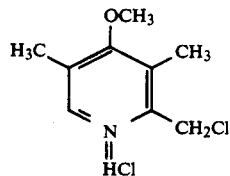

the process comprising:

acyloxylation of the 2-position methyl group of 2,3,5-trimethyl-4-methoxypyridine N-oxide of formula III

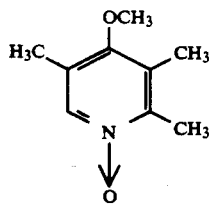

by treatment with an acylating agent in the presence of a catalyst, selected from 4-dimethylaminopyridine, 4-guanidinopyridine or 4-pyrrolidinopyridine, to obtain the compound of formula IVa

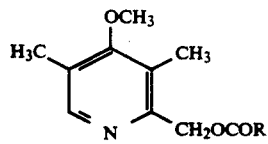

wherein R is methyl, trichloromethyl or trifluoromethyl;

basic hydrolysis of the formula IVa compound under mild conditions, carried out by adding an aqueous alkaline hydroxide solution having a pH between 11 and 13 in the presence of a cosolvent and at 0° to 75° C., to give 2-hydroxymethyl-3,5-dimethyl-4-methoxypyridine represented by the formula Va

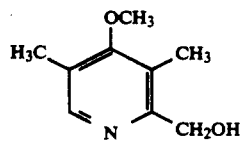

which is finally chlorinated with an amidinium chloride to give the 2-chloromethyl-3,5-dimethyl4-methoxypyridine hydrochloride.

2. A process according to claim 1, wherein said acylating agent is selected from acetic anhydride, trichloroacetic anhydride or trifluoroacetic anhydride.

3. A process according to claim 2, wherein said acylating agent is acetic anhydride with an excess thereof.

4. A process according to claim 1, wherein said cosolvent is selected from acetic acid, methylene chloride or chloroform.

5. A process according to claim 2, wherein when said acylating agent is trichloroacetic anhydride or trifluoroacetic anhydride, the reaction is carried out in an organochlorinated solvent under reflux temperature.

6. A process according to claim 5, wherein said organochlorinated solvent is chloroform.

7. A process according to claim 1, wherein said treatment with an acylating agent is carried out in the presence of a catalyst selected from 4-dimethylaminopyridine, 4-guanidinopyridine or 4-pyrrolidinopyridine.

8. A process according to claim 1, wherein said basic hydrolysis is carried out in the presence of a cosolvent at a temperature between 0° to 75° C.

9. A process according to claim 8, wherein said cosolvent is selected from methanol, ethanol or isopropanol.

10. A process according to claim 1, wherein said amidinium chloride is formed in situ by treatment of an amide with thionyl chloride.

11. A process according to claim 10, wherein said amide is selected from the group consisting of N,N-dimethylformamide, N,N-dimethylacetamide, tetramethylurea and acetamide.

12. A process according to claim 1, wherein the amount of said amide is selected from catalytic to stoichiometric.

* * * * *

UNITED STATES PATENT AND TRADEMARK OFFICE
CERTIFICATE OF CORRECTION

PATENT NO. : 5,292,886
DATED : March 8, 1994
INVENTOR(S) : Alberto Palomo Coll

It is certified that error appears in the above-identified patent and that said Letters Patent is hereby corrected as shown below:

On the title page, item (73):

The Assignee, "Esteve Quimica and Centro Genesis Para La Investigation, S.L." is missing.

Attorney, Agent or Firm - Bell, Seltzer, Park & Gibson is missing.

FOREIGN PATENT DOCUMENTS:

"0103353" should be -- 0103553 --.

Column 5, line 31, "describe" should be -- described --.

IN THE CLAIMS:

Column 8, line 25, ..."-dimethyl4-"... should be -- ...dimethyl-4-... --.

UNITED STATES PATENT AND TRADEMARK OFFICE
CERTIFICATE OF CORRECTION

PATENT NO. : 5,292,886

DATED : March 8, 1994

INVENTOR(S) : Alberto Palomo Coll

It is certified that error appears in the above-indentified patent and that said Letters Patent is hereby corrected as shown below:

Column 8, line 57, "1" should read --11--.

Signed and Sealed this

Twenty-eighth Day of June, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,292,886            Page 1 of 4
DATED      : March 8, 1994
INVENTOR(S): Alberto Palomo Coll It is certified that error appears in the above-indentified patent and that said Letters Patent is hereby corrected as shown below:

On the title page item [73] --Esteve Quimica, S.A. and Centro Genesis Para La Investigacion, S.L. --.

Column 1, lines 12-20, Formula I should appear as follows:

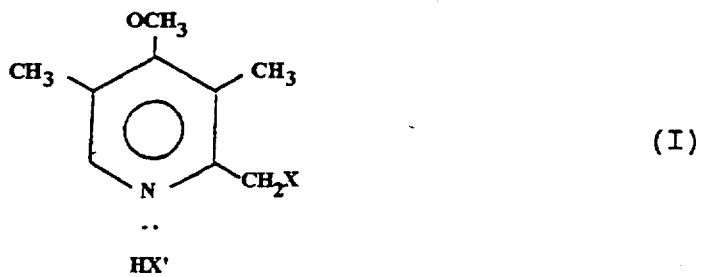

(I)

Column 1, lines 57-65, Formula IV should appear as follows:

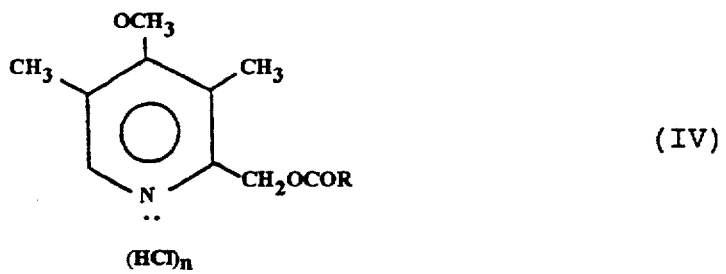

(IV)

UNITED STATES PATENT AND TRADEMARK OFFICE
CERTIFICATE OF CORRECTION

PATENT NO. : 5,292,886
DATED : March 8, 1994
INVENTOR(S) : Alberto Palomo Coll

It is certified that error appears in the above-indentified patent and that said Letters Patent is hereby corrected as shown below:

Column 2, lines 20-27, Formula IVb should appear as follows:

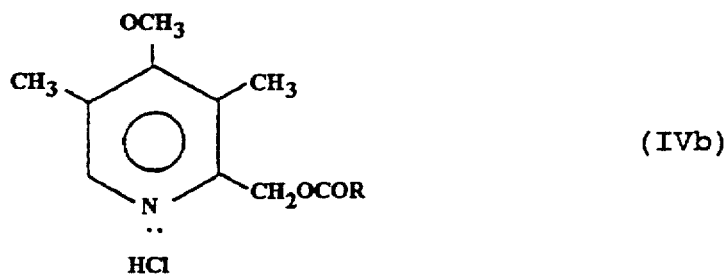

Column 2, lines 45-52, Formula VI should appear as follows:

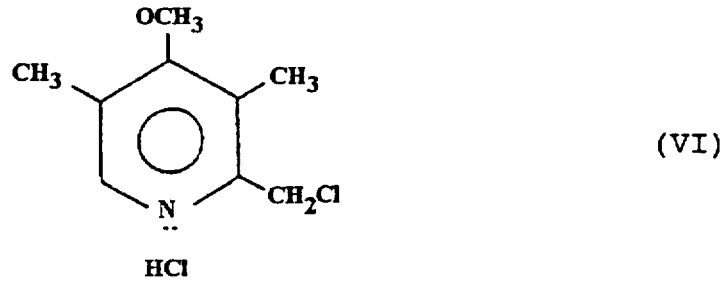

UNITED STATES PATENT AND TRADEMARK OFFICE
CERTIFICATE OF CORRECTION

PATENT NO. : 5,292,886

DATED : March 8, 1994

INVENTOR(S) : Alberto Palomo Coll

It is certified that error appears in the above-indentified patent and that said Letters Patent is hereby corrected as shown below:

Column 2, lines 59-66, Formula Vb should appear as follows:

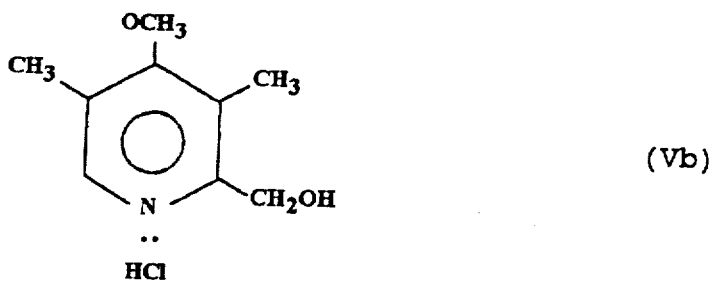 (Vb)

UNITED STATES PATENT AND TRADEMARK OFFICE
CERTIFICATE OF CORRECTION

PATENT NO.  : 5,292,886
DATED       : March 8, 1994
INVENTOR(S) : Alberto Palomo Coll It is certified that error appears in the above-indentified patent and that said Letters Patent is hereby corrected as shown below:

Column 7, lines 30-40, Formula VI should appear as follows:

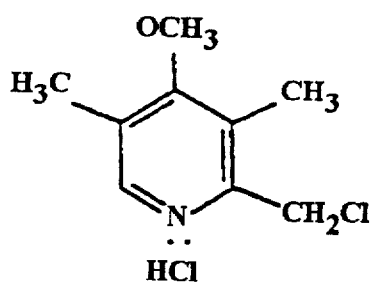

Signed and Sealed this

Eighteenth Day of October, 1994

Attest:

BRUCE LEHMAN

Attesting Officer

Commissioner of Patents and Trademarks